(12) United States Patent
Nakajima

(10) Patent No.: US 6,186,946 B1
(45) Date of Patent: Feb. 13, 2001

(54) URINALYSIS STICK FOR ANIMALS

(76) Inventor: Kenji Nakajima, 3-19-18, Mizukino, Moriyamati, Kitasouma-gun, Ibaraki (JP)

( * ) Notice: Under 35 U.S.C. 154(b), the term of this patent shall be extended for 0 days.

(21) Appl. No.: 09/469,778

(22) Filed: Dec. 22, 1999

(30) Foreign Application Priority Data

Mar. 19, 1999 (JP) .................................................. 11-075591

(51) Int. Cl.⁷ .............................. A61B 5/05; G01N 21/00; G01N 21/25; C12Q 1/58
(52) U.S. Cl. ........................... 600/362; 600/345; 422/58; 422/59; 356/421; 435/12
(58) Field of Search ..................................... 600/362, 300, 600/345, 361, 366, 551; 422/56–59, 61; 435/12; 356/421

(56) References Cited

U.S. PATENT DOCUMENTS

| | | | | |
|---|---|---|---|---|
| 4,523,852 | * | 6/1985 | Bauer | 356/421 |
| 5,137,692 | * | 8/1992 | Fritz | 422/61 |
| 5,160,979 | * | 11/1992 | Ota et al. | 356/423 |
| 5,160,980 | * | 11/1992 | Herpichboehm et al. | 356/423 |
| 5,183,742 | * | 2/1993 | Omoto et al. | 435/14 |

* cited by examiner

Primary Examiner—Cary O'Connor
Assistant Examiner—Nevin Natnithithadha

(57) ABSTRACT

A urinalysis stick for animals comprising a chemical reaction agent at an end, a color sample showing the discoloration stage at a rear end, and a half cut portion or a half fold portion provided in the middle of the stick for tearing off or folding the stick into half, so that an owner can easily examine urine of animals such as dog, cat and the like by himself/herself.

2 Claims, 3 Drawing Sheets

URINALYSIS STICK FOR ANIMALS

BACKGROUND OF THE INVENTION

1. Field of the Invention

The present invention relates to a urinalysis stick for animals which makes it possible for an owner of animals to easily examine the pH, protein, glucose, occult blood and the like in the urine of animals such as dog, cat and the like by himself/herself.

2. Description of the Related Art

A person can voluntarily collect his/her urine in a container such as a paper cup or the like. On the other hand, a dog or a cat will not discharge urine even if an owner orders it. Therefore, the owner has to wait until the animal shows a sign of urination, and collect urine rapidly in an instant of urination. In the case of a male dog which urinates outside by raising his one hind leg, it is possible to receive urine by inserting a paper cup in the crotch region. A female dog, however, squats to discharge urine, therefore, there is only a small gap between the ground, and it is not possible to insert a container for collecting urine in the crotch region. Similarly, both male and female cats trained to discharge in a pet toilet bowl in a room squat to discharge urine, therefore, it is not possible to collect urine by inserting a container in the crotch region.

Accordingly, the present inventor considered direct examination of urine instead of collecting urine. That is to say, a urinalysis stick for human urine make use of the animal urinalysis. In this manner, it should be possible to examine fresh urine promptly on the spot, by inserting the urinalysis stick in the crotch region of not only male dogs but also female dogs and cats.

On the actual trial, however, it was found that the commercially available urinalysis stick for a person was inconvenient unexpectedly. That is to say, the urinalysis stick for a person is separated a color sample showing the discoloration stage for judging the examination result from the stick. For instance, the color sample is only printed on the outside of a container for receiving the stick or on the outside of the package for receiving the container. Therefore, if an owner wants to examine the urine during a walk of a dog, he/she has to bring the urinalysis stick held in the container, or bring the color sample by tearing off from the package. Moreover, if the owner tries to receive the urinalysis stick wet by urine in a bag for droppings carried with him/her, the bag may be punctured by the end or rear end of the stick. In this case, clearing becomes a troublesome job.

OBJECTS AND SUMMARY OF THE INVENTION

It is therefore an object of the present invention to provide a urinalysis stick for animals which makes it possible for the owner to carry only one urinalysis stick when he/she takes out a dog outside or waits a cat going on the toilet bowl to examine urine.

The urinalysis stick for animals of the present invention comprises a coloring portion disposed a chemical reaction agent at an end, a judging portion disposed a color sample showing the discoloration stage at a rear end, and a half cut portion where the stick can be torn in two or a half fold portion where the stick can be folded in half in the middle of the stick.

In the coloring portion, a chemical reaction agent such as a coloring reagent is arranged by application, printing or impregnation or adhering a test paper. The coloring reagent to be used is not particularly limited, but for example, as for the pH examination, an indicator obtained by mixing methyl red and bromine thymol blue, having a coloration range of from pH 5 to 8 is preferable. Moreover, as for the protein examination, a protein reaction reagent composed mainly of tetrabromine phenol blue is preferable. Furthermore, as for glucose examination, a sugar reaction reagent composed mainly of glucose oxidase and peroxidase, or diaminofluorene dihydrochloride is preferable. Furthermore, as for examination of occult blood, cumene peroxyhydrate or tetramethylbenzine is preferable. According to the purpose of the examination, hold several kind urinalysis sticks for animals in piles in one hand, and bring them into contact with urine in such a manner that the coloring portion of each stick spread in a fan shape crosses the urine line during urination. The contact time with urine may be a moment. Moreover, in the above judging portion, a color sample showing the discoloration stage may be printed, or a color sample printed in color on a separate white paper may be adhered on the rear end of the stick.

After the coloring portion at the end of the stick has been brought into contact with the urine line during urination, the stick is torn in two at the half cut portion or the stick is folded at the half fold portion, to thereby place the judging portion provided at the rear end by the side of the coloring portion. In this manner, the color of the coloring portion colored or discolored due to the contact with fresh urine can be compared to the color sample in the judging portion placed side by side at one glance. Therefore, the examination result can be judged immediately on the spot.

The urinalysis stick for animals of the present invention has a size capable of being held with fingers, therefore it can be put in a pocket or the like and carried for a walk of a dog. Moreover, after examination, it can be cut into half or folded in two to put into a plastic bag or the like for receiving droppings of the dog, hence there is no possibility of breaking through the bag by the end of the stick. Therefore, this bag can be brought back home and thrown out as the kitchen refuse, and can be cleared easily. Similarly, it can be used for the pet toilet bowl for a cat in the room. It is desirable to produce the urinalysis stick for animals of the present invention from woods, bamboo or cardboard, so that it can be disposed of by burning as the kitchen refuse together with the contaminated paper, sand and feces. It is also desired to use cheap recycled papers instead of expensive cardboard, because it is thrown away after single use.

BRIEF DESCRIPTION OF THE DRAWING

The features, objects and advantages of the present invention will become more apparent from the detailed description described below of the preferred embodiments of the present invention when taken in conjunction with the drawings, wherein.

DETAILED DESCRIPTION OF THE PREFERRED EMBODIMENTS

Figure 1:
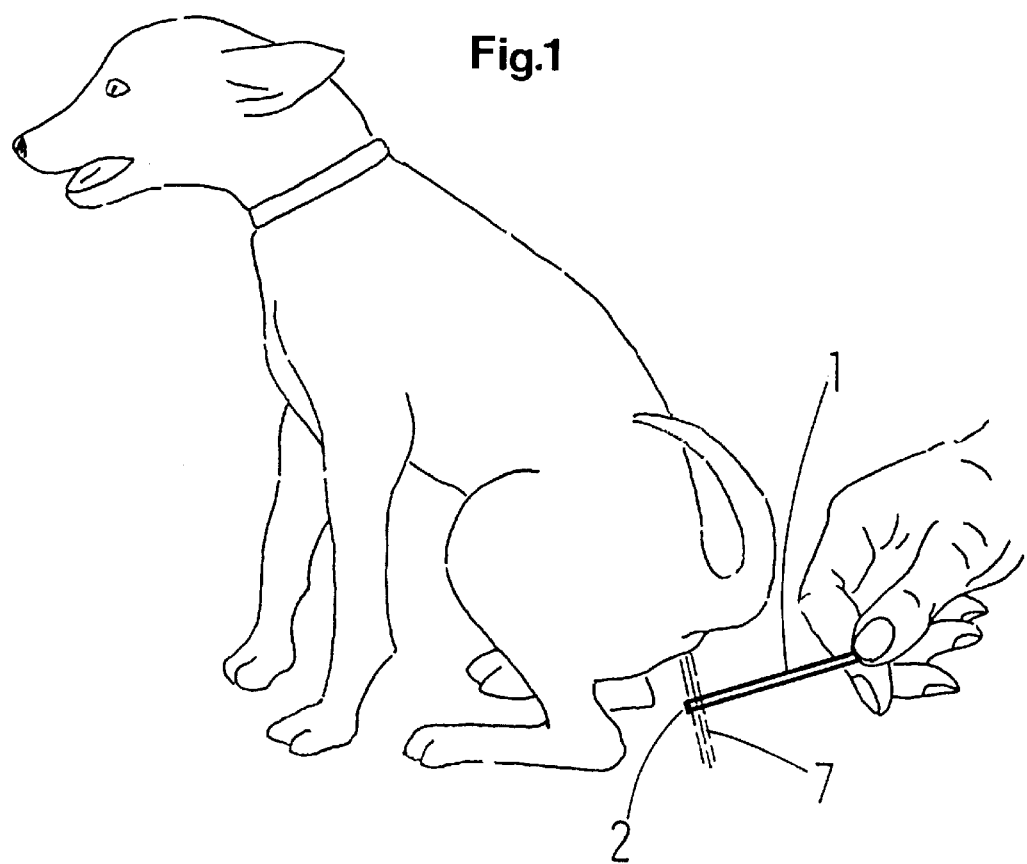
FIG. 1 is a diagram showing the state of use of a urinalysis stick for animals of the present invention.

When a urinalysis stick for animals of the present invention is used for a female dog, as shown in FIG. 1, the urinalysis stick 1 held with fingers is inserted in the crotch region of the female dog which has a habit of discharging urine by squatting, while holding the hip slightly above the ground, to thereby bring the coloring portion 2 at the end into contact with the urine line 7. The similar method as in FIG. 1 can be applied to male cats and female cats which have the same habit of discharging urine by squatting, for examining urine easily. Moreover, though not shown, even for male dogs which discharge urine by raising one hind leg, the urinalysis stick can be insert between the crotch to easily bring the coloring portion into contact with the urine line.

Figure 2:
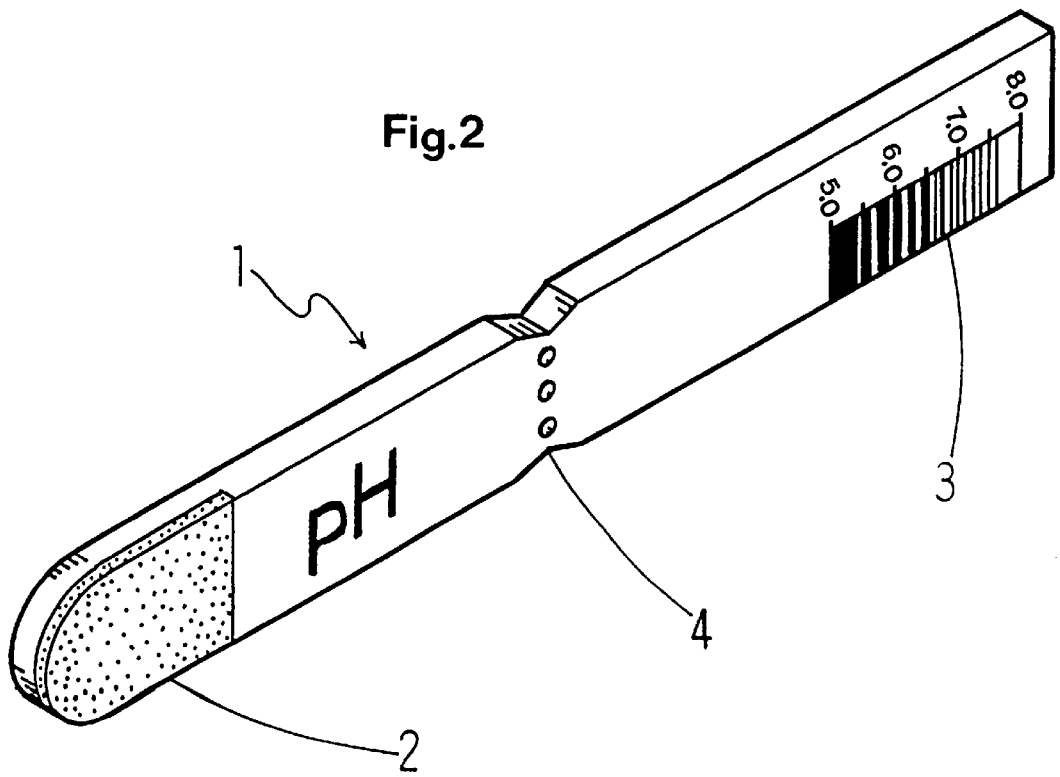
FIG. 2 is a perspective view showing a first embodiment of a urinalysis stick for animals of the present invention.

FIG. 2 is a perspective view showing a first embodiment of a urinalysis stick for animals of the present invention, and illustrates a stick for the pH examination which is most frequently used. The size of the urinalysis stick 1 made of a cardboard is preferably 15 cm in length, 1 cm in width and 3 mm in thickness, but for cats and small dogs, the length may be shorter, for example, 10 cm. The coloring portion 2 at the end is provided with a difference in level so that the test paper is not peeled off, and a commercially available methyl red-bromine thymol blue mixed test paper is adhered thereto. The length of the coloring portion is preferably about 2 mm. To the judging portion 3 at the rear end is printed a color sample having a discoloration range corresponding to the pH test paper, and a scale of from pH 5 to pH 8 is displayed on the side. The interval of the scale shown in the figure is 0.5, but it is desired to make the scale interval to be 0.2 for the product. Moreover, in the middle of the urinalysis stick 1, there is provided a half cut portion 4 comprising a pair of incisions on the right and left sides and a plurality of holes.

Figure 3:
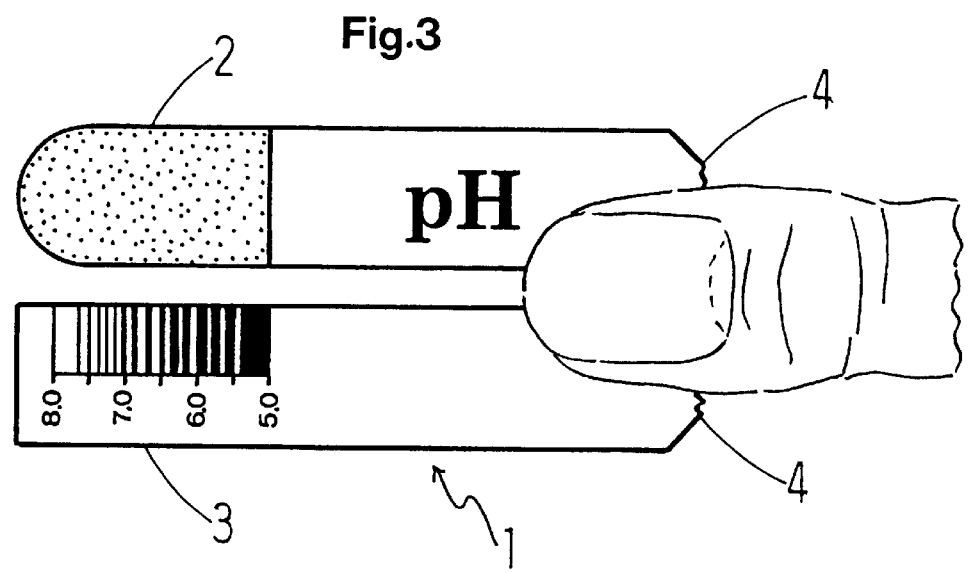
FIG. 3 is a plan view showing the state of use of the embodiment in FIG. 2.

When this urinalysis stick 1 is used, after the coloring portion 2 is dampened with urine, the half cut portion 4 is torn off with fingers. Then, as shown in FIG. 3, the coloring portion 2 discolored due to the contact with urine and the judging portion 3 on the other side are placed in parallel, to judge the pH rapidly before the coloring portion 2 is dried. In this manner, accurate pH of fresh urine can be examined on the spot. Other examinations of protein, glucose and occult blood are performed in the similar manner.

Figure 4:
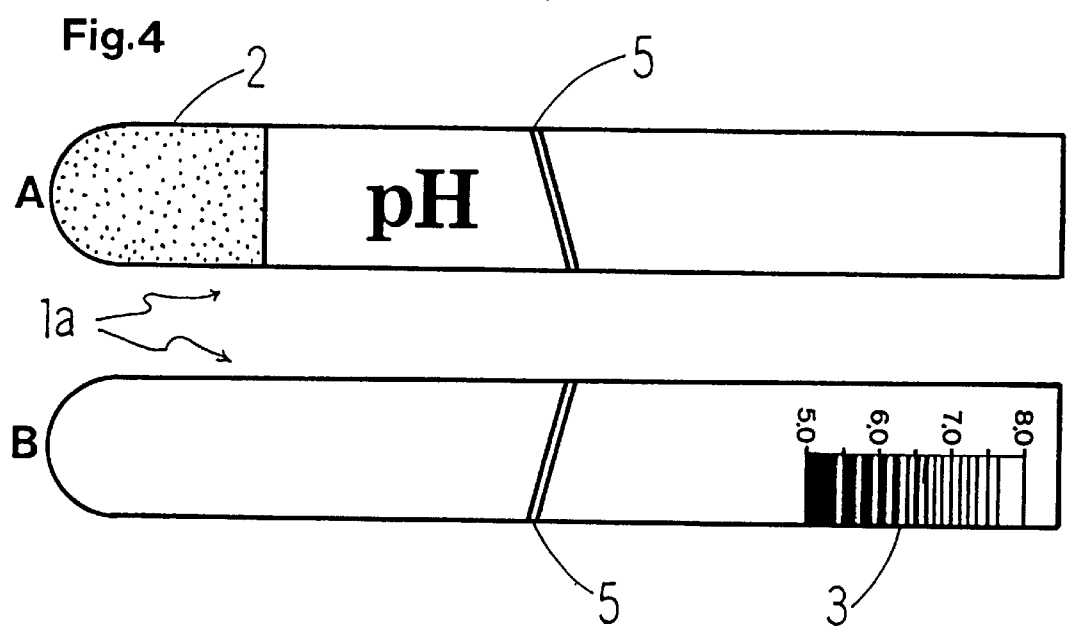
FIG. 4 is a plan view showing a second embodiment of a urinalysis stick for animals of the present invention.
Figure 5:
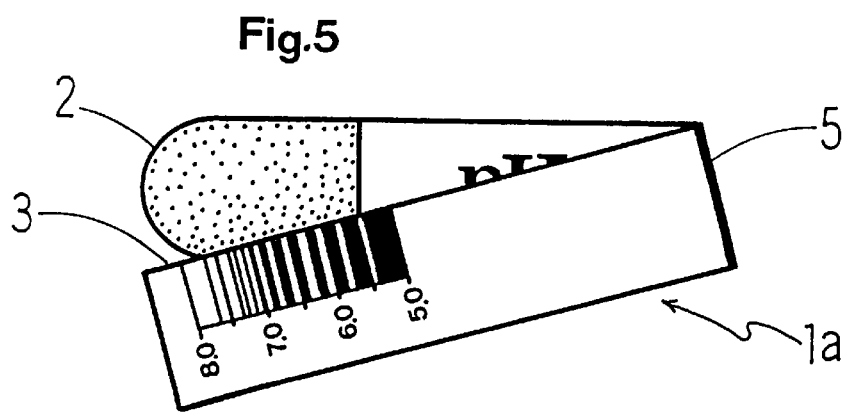
FIG. 5 is a plan view showing the state of use of the embodiment in FIG. 4.

FIG. 4 is a plan view showing a second embodiment of the urinalysis stick 1a made of a cardboard, and a pH indicator is applied or printed on the surface at the end of the face side A to form the coloring portion 2, and a color sample and a scale are printed on the surface at the rear end of the back side B to form the judging portion 3. Then, a half fold portion 5 made for being easily folded down obliquely is provided in the middle of the urinalysis stick 1a. When the urinalysis stick 1a is obliquely folded down, after the coloring portion 2 is brought into contact with urine, as shown in FIG. 5, the judging portion 3 printed on the back side B appears at the side of the coloring portion 2. Therefore, it is easy to compare the color of the coloring portion 2 discolored due to the contact with urine with the color sample of the judging portion 3.

Figure 6:
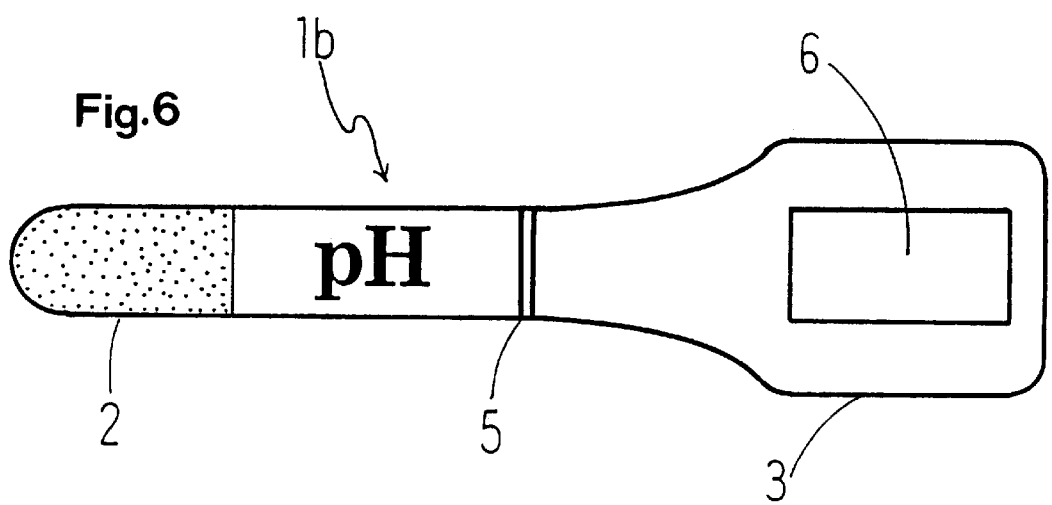
FIG. 6 is a plan view showing a third embodiment of a urinalysis stick for animals of the present invention.
Figure 7:
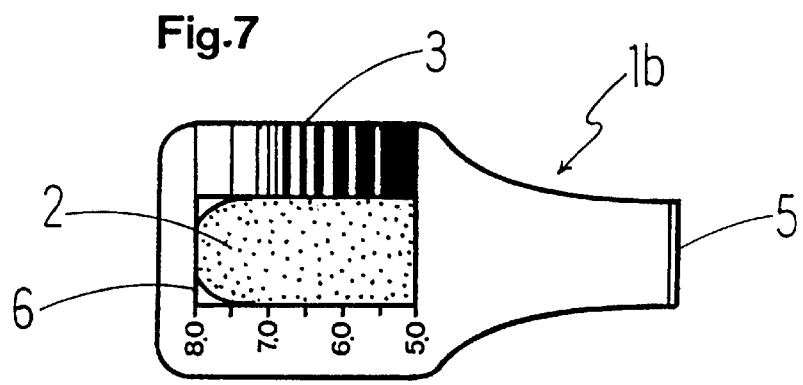
FIG. 7 is a plan view showing the state of use of the embodiment in FIG. 6.

FIG. 6 is a plan view showing a third embodiment of the urinalysis stick 1b, and the half fold portion 5 is provided at right angles to the longitudinal direction of the stick, and the judging portion 3 is provided with a window 6. When the stick 1b is folded down at the half fold portion 5, as shown in FIG. 7, the coloring portion 2 appears from the window 6, to make the comparison with the color sample easy.

Figure 8:
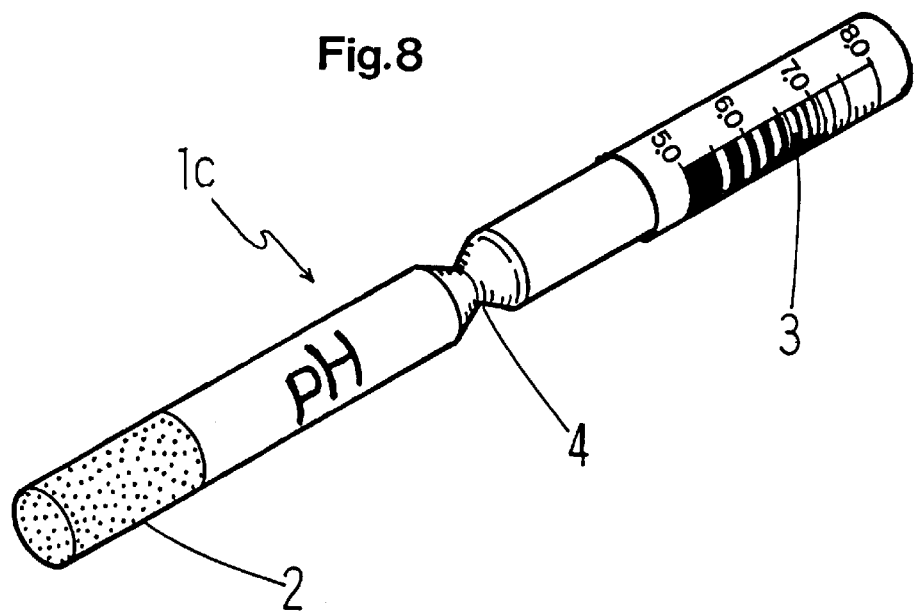
FIG. 8 is a perspective view showing a fourth embodiment of a urinalysis stick for animals of the present invention.

FIG. 8 is a perspective view showing a fourth embodiment of the urinalysis stick 1c. A wood, bamboo, synthetic resin or the like is molded in a log shape, and a half cut portion 4 is provided in the middle thereof. As the coloring portion 2, an absorptive fiber bundle is attached to the tip end of the stick, and impregnated with a coloring reagent. Alternatively, a commercially available test paper may be wrapped thereon. As the judging portion 3, a color sample printed on a white paper is wrapped on the rear end of the stick.

As is obvious from the above description, according to the urinalysis stick for animals of the present invention, since the judging portion arranged with the color sample at the rear end is provided, at the time of examining urine of a dog during a walk, one stick has only to be carried. Moreover, since a half cut portion or a half fold portion is provided in the middle, the stick can be torn off or folded into two to thereby place the coloring portion at the front end and the judging portion at the rear end side by side. Hence, the difference in color at the both portions can be compared at a glance, giving an advantage that the examination result of fresh urine can be known immediately on the spot. Furthermore, the urinalysis stick used and folded or bent into half during a walk can be put into a plastic bag or the like together with feces of the dog and disposed of, hence clearing becomes easy.

What is claimed is:

1. A urinalysis stick for animals comprising:
    (a) a coloring portion arranged with a chemical reaction agent at an end on the face side of the urinalysis stick;
    (b) a judging portion arranged with a color sample showing the discoloration stage at a rear end on the face side of the urinalysis stick; and
    (c) a half cut portion for tearing off the urinalysis stick into half or a half fold portion for folding the urinalysis stick into half, provided in the middle of the urinalysis stick.

2. A urinalysis stick for animals comprising:
    (a) a coloring portion arranged with a chemical reaction agent at an end on the face side of the urinalysis stick;
    (b) a judging portion arranged with a color sample showing the discoloration stage at a rear end on the back side of the urinalysis stick; and
    (c) a half cut portion for tearing off the urinalysis stick into half or a half fold portion for folding the urinalysis stick into half, provided the middle of the urinalysis stick.

* * * * *